United States Patent [19]

Walsh

[11] Patent Number: 5,057,502

[45] Date of Patent: * Oct. 15, 1991

[54] COMPOSITION AND TOPICAL AND SYSTEMIC TREATMENTS OF CONDITIONS CAUSED BY HEAVY, OILY OR GREASY SECRETIONS

[76] Inventor: William E. Walsh, 990 Lydia Dr., Roseville, Minn. 55113

[*] Notice: The portion of the term of this patent subsequent to Feb. 6, 2007 has been disclaimed.

[21] Appl. No.: 475,717

[22] Filed: Feb. 6, 1990

Related U.S. Application Data

[63] Continuation-in-part of Ser. No. 57,166, Jun. 2, 1987, Pat. No. 4,898,852.

[51] Int. Cl.$^5$ ............................................... A61K 7/00
[52] U.S. Cl. ....................................... 514/54; 514/859; 514/58; 514/951; 514/944; 424/DIG. 5; 424/45; 424/46; 424/489; 424/195.1; 536/103
[58] Field of Search ............ 424/195.1, 45, 46, DIG. 5, 424/489; 514/54, 58, 859, 951, 944; 536/103

[56] References Cited

U.S. PATENT DOCUMENTS

| | | | |
|---|---|---|---|
| 4,247,533 | 1/1981 | Lewis et al. | 514/58 |
| 4,306,021 | 12/1987 | Dolak et al. | 435/128 |
| 4,352,794 | 10/1982 | Koch | 514/58 |
| 4,569,839 | 2/1986 | Grollier et al. | 424/195.1 |
| 4,593,046 | 6/1986 | Gruber | 514/717 |
| 4,609,674 | 9/1986 | Gupte | 514/547 |
| 4,634,436 | 1/1987 | La Tour | 424/195.1 |
| 4,640,932 | 2/1987 | Fong et al. | 514/714 |
| 4,659,701 | 4/1987 | Wuest et al. | 514/130 |
| 4,664,910 | 5/1987 | Caserio et al. | 424/70 |
| 4,668,664 | 5/1987 | Rougier et al. | 514/29 |
| 4,671,956 | 6/1987 | Bouillon et al. | 424/59 |
| 4,677,120 | 6/1987 | Parish et al. | 514/549 |
| 4,692,329 | 9/1987 | Klein et al. | 424/81 |
| 4,734,403 | 3/1988 | D'Hinterland et al. | 514/54 |
| 4,738,956 | 4/1988 | Scott et al. | 514/179 |
| 4,743,400 | 5/1988 | Maryanoff | 260/408 |
| 4,758,432 | 7/1988 | Yeung et al. | 424/195 |
| 4,762,847 | 8/1988 | Edwards et al. | 514/336 |
| 4,826,681 | 5/1989 | Jacquet et al. | 424/613 |
| 4,826,969 | 5/1989 | Maignan et al. | 536/55.2 |
| 4,839,159 | 6/1989 | Winter et al. | 424/59 |
| 4,857,525 | 8/1989 | Philippe et al. | 514/277.5 |
| 4,898,852 | 2/1990 | Walsh | 514/54 |

OTHER PUBLICATIONS

S. Joveva et al., Chemical Abstracts Mar. 3 (1986), vol. 104, p. 594, abstract 104:67794w.
B. Casu et al., Carbohydrate Research, 63, 13–27 (1978).
Tjan et al., Carbohydrate Research, 34, 15–32 (1974).
Daniel W. Armstrong and Weiyong Li, Optimization of Liquid Chromatographic Separations on Cyclodextrin-Bonded Phases, Chromatography, Mar. 1987, pp. 43–47.
Federal Register, vol. 50, No. 10, Tuesday, Jan. 15, 1985, proposed Rules, 21 CRF Part 333, Part V. Department of Health and Human Services, Food and Drug Administration.
Henry H. Roenigk, Jr., M. D., Retinoids, Department of Dermatology, Northwestern University Medical School, Chicago, IL, cutis, vol. 39, APr. 1987, pp. 301–305.
Kirk-Othmer Encyclopedia of Chemical Technology, vol. 15, 2nd Edition (1968), pp. 112–132.
Aldrich Chemical Company, Inc. Technical Bulletin, Aldrich Fine Chemicals, pp. 373–374.
Markkanen et al., "Antiherpetic Agent from Juniper Tree (Juniperus Communis), Its Purification, Identification, and Testing in Primary human Amnion Cell Cultures," Drugs Exptl. Clin. Res. VII(5) 691–697 (1981).
Translation of S. Joveva et al., "Feasibility of Using Thin-Layer Chromatography to Determine Carbohydrates in the Juniper Berry," (Chemical Abstracts 104:67794W) No. 9, Mar. 3, 1986.

*Primary Examiner*—Ronald W. Griffin
*Attorney, Agent, or Firm*—Merchant, Gould, Smith, Edell, Welter & Schmidt

[57] ABSTRACT

Novel juniper extract materials, having some surfactant properties and other properties, are useful in the thinning of heavy oily, greasy secretions and giving symptom relief in human acne and other conditions of thickened secretions and can be used in a variety of treatment modes, both topical and systemic.

19 Claims, No Drawings

COMPOSITION AND TOPICAL AND SYSTEMIC TREATMENTS OF CONDITIONS CAUSED BY HEAVY, OILY OR GREASY SECRETIONS

This application is a continuation-in-part of Ser. No. 057,166, filed June 2, 1987, now U.S. Pat. No. 4,898,852.

FIELD OF THE INVENTION

The invention relates to novel extract compositions and their use topically in cosmetic or palliative treatment of human skin and hair and systemically in other conditions. More particularly, the invention relates to novel extract compositions that can be used topically in the form of a spray, topical liquid, topical gel or cream, ointment or mask, a composition that can be nebulized, or a composition in the form of a compressed or flowable powder. More particularly, the invention relates to a novel dermopharmaceutical composition that has shown particular value in the cosmetic or palliative treatment of thick oily or greasy skin secretions with beneficial effects in acne or other related dermal lesions. It also relates to methods of isolating this extract.

BACKGROUND OF THE INVENTION

Acne (acne vulgarous) is a chronic disorder of the skin generally confined to face, neck, chest, and back. Primary acne lesions appear as horny plugs (blackheads) which later can develop into pink papules, pustules, or nodules. The nodules can be tender, acute, localized collections of pus deep in the dermis. Large pustular lesions may develop and break down adjacent tissues to form lakes of pus, sinuses and, in certain cases, characteristic pitted scars. Tests have shown that heredity is a major predisposing factor in the disease which is described as polygenic (some defects are caused by a group of genes) and is difficult to clearly delineate heredity effects. Acne typically has a puberty or post-puberty onset wherein pilosebaceous units enlarge and produce sebum. Acne can occur when an excess of sebum is produced or when the folicular openings are too small to permit the escape of increased sebum flow, or when sebum is too thick to be expelled from the folicular openings, or under all three conditions. The duration of acne vulgarous after onset is highly variable and can persist into and through the fourth decade of life, but typically peaks during the teen years and typically terminates in the third decade of life. A number of different treatments have been proposed, however, none have met with uniform success.

Clearly a substantial need exists for effective treatments of acne and related skin disorders that can reduce or alleviate the unsightly aspect of the skin disorder.

BRIEF DISCUSSION OF THE INVENTION

I have discovered a novel cosmetic or palliative dermopharmaceutical composition for treatment of human skin and hair disease.

I have also found that the administration of one or more of the compositions of the invention to human patients having a skin disorder can provide some relief of symptoms including removal of blackheads, reduction in size of acne lesions, improving the flow characteristics of sebum, and improved rates of healing. I have also found that other human hair and skin diseases can be effectively treated.

The formulations of the anti-acne treatment compositions of the invention can take the form of a powder or compressed powder, a topical liquid, a topical gel, a topical spray, or a mask-like material. Such materials can be dispersed or suspended in an aqueous, organic or inorganic medium.

DETAILED DISCUSSION OF THE INVENTION

The novel cosmetic and dermopharmaceutical compositions of the invention that I have developed for the treatment of human skin and hair disease comprise, typically, an extract of the plant source containing the cyclopolysaccharic acid. The compound or the extract can be combined in a medium for application to the human body with other active compositions (anti-acne or otherwise) that can cooperate with the cyclopolysaccharic acid compound or extract to treat human hair and skin.

The cyclopolysaccharic acids of this invention can be an extract obtained from natural sources.

I have found that the cyclopolysaccharic acid compound can be obtained by fractionation of plant sources. I have found that the compounds of the invention occur naturally in relatively high concentration, particularly in juniper berries. The term "saccharic acid" in this invention means a mono saccharide in a furanose or pyranose ring structure having a carboxyl group, preferably, the 6-carbon atom is in the form of a carboxyl group. Saccharic acids that can be included in the cyclic polymers of the invention include α-D-glucopyranosic acid, α-D-mannopyranosic acid, α-D-fructofuranosic, other similar acids and mixtures thereof, said acids having the following formulae:

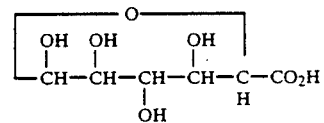

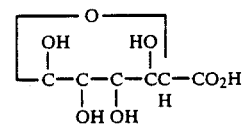

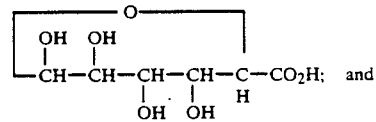

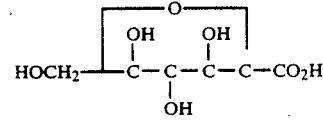

Such polymers are typically formed by (1→4), (2→4), (1→3), (2→3) linkages between the monosaccharic acid units to form the cyclic polymer.

The preferred cyclopolysaccharic acid comprises a molecule made of a 6 carbon cyclopyranose saccharic acid. The most preferred compound comprises a molecule of the formulae:

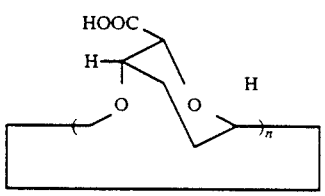

wherein n is greater than 4 and preferably n is an integer of 5 to 10. The most preferred compound is a cyclopolygalacturonic acid compound of the invention which comprises a cyclobeta-D-(+) polygalacturonic acid having 5 or galacturonic acid units of the formula:

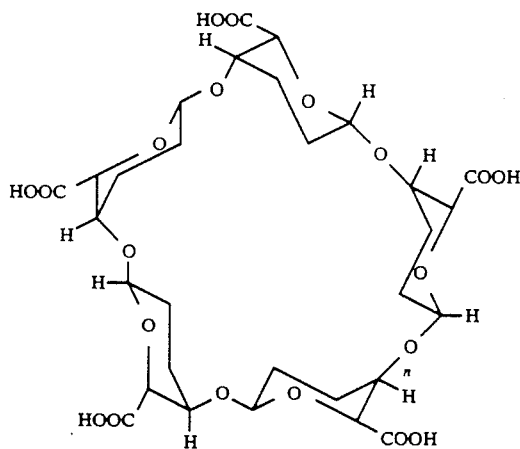

wherein n=1 to 4.

The most preferred cyclopolygalacturonic acid compositions of the invention are preferably obtained from natural crushed or ruptured juniper berry sources through a hot aqueous extraction from the natural source. A subsequent purification of the material can be used if desired for reasons related to product appearance.

In somewhat greater detail, the preferred compounds of the invention can be obtained from crushed presoaked berries using a 24-hour boiling water Soxhlet extraction procedure utilizing 1200 milliliters of water and 200 grams of the crushed berries. Typically, the initial extraction procedure results in 1 to 2 grams of semipurified material containing the active cyclopolygalacturonic acid compounds. At least a 24-hour extraction appears to be required to fully extract active material from the source. Further, the presoaking period appears to permit natural enzyme action which appears to make the cyclopolygalacturonic acid compounds more available to boiling water extraction. After the aqueous extraction is complete, an acidified (pH 3-5) aqueous preparation of the compound is extracted with moderately polar organic solvents to remove small amounts of natural fats and oils in the aqueous extract. The fat-free aqueous concentrate is separated into components using a chromatographic component separation. I have found that reverse-phase chromatography provides purest active material. In this technique, constituents are separated according to their relative hydrophobicity (or polarity) and tested for activity. The reverse phase chromatography enables the ready separation of simple sugars from the aqueous solution by elution while retaining the materials of mixed polarity including the cyclopolygalacturonic acids. A later elution with a methanol/water cosolvent material (typically greater than 40 volume % methanol) successfully elutes the cyclopolygalacturonic acid compositions. After elution, active material can be precipitated by addition of methanol to a concentrated aqueous extract. After precipitation, subsequent reverse-phase chromatography can be applied to reduce the free monocarbohydrate or oligosaccharide content of the cyclopolygalacturonic acid fractions. It is clear that, using these procedures, relatively purified cyclopolygalacturonic acid compounds have been obtained in view of the compound characterization that follows.

In extracting the cyclopolygalacturonic acid components of the invention, it became apparent that the components' ability to hold strongly to the solids of the juniper berry material, glass containers, and filtering materials must be defected to allow recovery of the components in the filtrates. It was found that boiling crushed juniper berries in 50%/50% isopropyl alcohol-water, acidifying with 4% aqueous, acetic acid, and adding an aqueous 2% surfactant, allowed good recovery of the active principle of juniper berries when the resultant mixture was filtered without cooling the boiling mixture.

The following description of the compounds of this invention examines the product of the purified extraction procedure.

The molecular structure assigned to the active class of compounds of the invention has been obtained using spectroscopic analysis, elemental analysis, chemical enzyme and enzymatic modification, interpretation of chromatographic behavior, and observation of the effects of the composition on the surface tension of aqueous solutions. I have concluded that the biologically active molecule is an acidic polysaccharide, related to pectin (a linear polygalacturonic acid). No evidence of active fatty acids or hydrocarbon glycosides (i.e., saponin or otherwise), or a nitrogen-containing material (an amino acid or an amino sugar) is shown. Nuclear magnetic resonance spectroscopy, both proton and carbon ($^1$H- and $^{13}$C-spectroscopy), support a carbohydrate structure with no aliphatic or aromatic hydrocarbon substituents. Infrared analysis supports the polyhydroxy structure. Elemental analysis shows that elements other than carbon, hydrogen and oxygen appear to be absent. From acid base reactions, the material appears to have an acidic functionality and, through reaction with commercial pectinase preparation, the composition appears to comprise a polygalacturonic acid sequence. A cyclic structure is suggested by its tendency to associate with a variety of compounds and surfaces.

The presence of carboxylate groups on the molecule suggests the possibility that the compound may be absorbed directly in the stomach (at low pH, suppression of dissociation of the proton maximizes direct absorption into the lining of the stomach). This characteristic would be advantageous in that effective levels in blood could be achieved through oral administration instead of cumbersome intravenous injection in humans. Indeed, I have found that oral ingestion of the compound resulted in promoting the mobilization and the expulsion of the thick inspissated secretions of sinus congestion and asthma.

In addition to the unique cyclopolygalucturonic acid compound and other active acne treatment compounds, the compositions of the invention can include any cosmetic vehicle which does not reduce the properties of the active materials of the composition. Such ingredients, which can be used in the topical treatment and compositions of the invention to provide aesthetic and cosmetic benefits and to facilitate administration and treatment, include emollients, such as hydrocarbon oils and waxes, lanolin and lanolin derivatives, silicone oils, triglyceride esters, fatty acids, fatty alcohols, alkyl and alkenyl esters of fatty acids, polyhydric alcohols, polyester derivatives, and wax esters and beeswax derivatives. Such emollients preferably comprise from 10 percent to as much as 90 percent of the compositions. Such materials can act as the diluent or base into which the active ingredients are blended for treatment.

A desirable class of emulsifiers used in the compositions of the invention, which can be used in amounts of from 1 to 10 percent or more of the compositions, include many natural emulsifiers such as fatty acid monoglycerides, fatty alcohols, polyethylene glycols, propylene glycols, and polypropylene glycols, anionic emulsifiers, such as alkyl ethoxy ether sulfonates, ammonium alkyl sulfates, and fatty acid soaps; and cationic emulsifiers, such as quaternary ammomium, morpholinium, and pyridinium compounds.

Chelating agents such as EDTA (ethylene diamine tetraacetate acid), nitrilotriacetic acid, gluconic acid, citric acid, and tartaric acid, and salts thereof, preferably at a low of 0.1 to 5 weight percent of the compositions may be used to reduce the effect of metal ions on the decomposition of any active ingredient in the material.

Optional ingredients used in the treatment compositions of the invention include highly divided sulfur (USP grade) at a level of 1–15 weight percent, thickening agents such as polyacrylic acid, crosslinked carboxyl polyethylene polymers, tragcanth gum, kharava, and polyethylene glycols at a level of about 1–5 percent of the compositions. Trace amounts of fragrance materials, such as perfumes and dyes, can be used. The composition can be diluted with water or other volatile or nonvolatile solvents or diluents to obtain the desired viscosity.

The treatment compositions can be a topical powder-treatment material. Such powder-treatment materials typically contain 0.1 to 10 weight percent of the extract material containing the cyclopolygalacturonic acid compounds of the invention in conjunction with other anti-acne materials in a solid powder or powder stick. The powder or powder-stick material is developed by blending the active ingredients into a powder support which can then be packaged as a free-flowing, easily-applied powder, or compressed into a stick which can be rubbed onto the effected area for treatment. The powder absorbent is a powdered substance which will function when applied to the skin, in particular on the face, in absorbing excess moisture derived from sebaceous secretions and perspiration. The combined effect of the active anti-acne ingredients of the invention, in conjunction with the powder, reduces the impact of build-up of liquid materials derived from sebacious secretions on the skin and obtains acne treatment from the anti-acne compositions. Such a cooperative combination achieves its desired or proper balance of cleanliness and anti-acne properties, avoiding either greasy or excessively dry skin. The powder-absorbent material should have the ability to absorb at least twice its weight of oil, or at least its own weight in aqueous moisture. The particle size of the powder material is not critical with respect to its treatment capacity, however, the particle size could not exceed one hundred microns, and should have particle size ranging from 10 to 90 microns to increase its cosmetic acceptability and anti-acne properties. Preferred powder absorbent compositions include urea formaldehyde foam materials, fumed silica, magnesium carbonate, magnesium oxide, kieselguhr, kaolin, talc, starch, titanium dioxide, zinc oxide, clays, including smectites, montmorillonite, hectorite, and others; dry protein powders, including dried collagen; and anionic polyelectrolytes, such as crosslinked etherified starch, polyacrylic acid, polyamide/epichlorohydrin materials, etc.

The simplest topical preparation of the anti-acne material of the invention is a powdered admixture. A suitable exemplified preparation is as follows:

| Ingredient | Percentage |
| --- | --- |
| Juniper Extract | 1% |
| Benzoyl peroxide | 1–10% |
| Powder Base | Balance |

The above ingredients can be intimately mixed and dusted onto an affected skin area from 1 to 4 times daily. The powder can be compressed into a compact or stick.

If a liquid preparation is desired, the following is a simplified composition which can be made and applied from 1 to 4 times daily as a lotion.

| Ingredient | Percentage |
| --- | --- |
| Juniper Extract | 1% |
| Erythromycin | 1 wt % |
| Ethanol diluent | QS |

Other examples which are representative of the invention are a lotion which can be prepared as follows:

| Ingredient | Percent |
| --- | --- |
| Hydrocortisone | 0.5 wt % |
| Juniper Extract | 0.5 |
| Fatty alcohol | 25.5 |
| Polyethylene glycol molecular weight 1,000 | 5.0 |
| Preservatives | 0.7 |
| Volatile vehicle | 67.8 |

A cream material can be prepared as follows:

| Ingredient | Percent |
| --- | --- |
| Ethoxylated fatty alcohol | 15.0 |
| Fatty alcohol | 1.25 |
| Isopropylmyrstate | 5.0 |
| Preservatives | 0.1 |
| Polyoxyl 40 stearate | 0.25 |
| Deionized water | 60.3 |
| Propylene glycol | 3.0 |
| Benzoyl peroxide | 4.0 |
| Juniper Extract | 1.0 |
| Acetone | 10.0 |
| Dioctyl sodium sulfosuccinate | 0.1 |

A suitable, simplified preparation of a gel-topical treatment material is as follows:

| Ingredient | Percent |
| --- | --- |
| Deionized water | 55.65 |
| Colloidal Bentonite | 2.5 |
| Polyacrylic acid | 1.0 |
| Dioctyl sodium sulfosuccinate | 1.0 |
| Diisopropynol amine | 0.75 |
| Ethyl alcohol | 34.0 |
| Butylated hydroxy anisoles | 0.1 |
| 13-cis-retinoic acid | 2.5 |
| Juniper extract | 2.5 |

Materials Useful in Combination with the Cyclopolygalacturonic Compounds of the Invention Retinol (Vitamin A) and retinoic acid (Vitamin A acid) and its isomers and certain of its analogs can have beneficial effects in the treatment of acne and other hair and skin disorders. A variety of retinol and retinoic acid compounds are known, however, 13-cis-retinoic acid is preferred for treatment of cystic and conglobate acne.

The novel treatment compositions of the invention can contain an erthyromycin composition including erythromycin, A, B or C. These typically differ in the carbohydrate portions of the molecule. A variety of other erythromycin groups are known, including erythromycin estole, erythromycin glucoheptone, erythromycin lactobionate, erythromycin propionate, erythromycin stearate, and others.

Aloe vera has been identified as being an effective anti-irritant in the treatment compositions of the invention. U.S. Pharmacopeae identifies aloe as the dried latex of the leaves of the plant aloe barbadensis. The chemistry of aloe vera has been investigated over the past few years, however, the compositions of aloe vera have not been fully elucidated. Aloe vera apparently includes polysaccharides, enzymes, trace sugars, calcium oxalate, proteins, hormones, trace metals and other compositions.

The following table contains a number of active pharmaceutical agents that can be used to obtain a cooperative treatment effect with the compositions of the invention.

| Ingredient | Typical Concentration | Effect |
| --- | --- | --- |
| Coal Tar Extract | 1-5% | Psoriasis Treatment |
| Allantoin | 0.1-1% | Skin Treatment |
| Glycerin | 1-10% | Skin Treatment |
| Camomile Extract | 1-5% | Anti-Itch Treatment |
| Butabenpicrate | 1-5% | Anesthetic |
| Providone-Iodine | 1-5% | Antiseptic |
| Bactimycin | 0.1-1% | Antibiotic |
| Diethyltoluamide | 1-10% | Insect Repellant |
| Papain | 0.1-1% | Psoriasis |

Application and Dosage

I have shown that cyclopolygalacturonic acids possess anti-acne and antifacial lesion activity in human subjects. The effective dosage of the cyclopolygalacturonic acids is about 0.001 to 50 milligrams, preferably about 0.01 to 5 milligrams, per kilogram of body weight and is appliable to human subjects in topical form, as a powder, liquid, gel spray, lotion, cream, etc. The treatment formats of the compositions of the invention can contain inert fillers, enabling the manufacturer to readily dispense the compositions in active form with inert fillers include lactose, mannitol, sucrose, calcium sulfate, calcium phosphate, microcrystalline cellulose gums, methyl cellulose, cornstarch, alginic acid, stearic acid, magnesium stearate, carbowax, and others.

The following Examples are provided to support an understanding of the invention and to include a best mode.

EXAMPLE 1

205 grams of juniper berries were crushed and soaked in distilled water for 2 weeks. The soaking water was removed and the crushed berries were placed in a large scale Soxhlet extraction apparatus (said apparatus containing a condenser, extractor and a heated round bottom flask) containing 1200 milliliters of distilled water. Heating was initiated and a boiling water extraction continued for 24 hours. The aqueous Soxhlet extract was removed from the Soxhlet extractor and extracted twice with ethyl acetate (2400 milliliters and 1600 milliliters aliquots). The organic layer was separated and discarded. The aqueous phase was placed in a 4 liter Erlenmeyer flask and into the aqueous composition was placed 3000 milliliters of methanol. A precipitate was formed which was filtered. The methanolic solution was evaporated. The total material obtained in the filtrate and the residue after evaporation totalled 14.72 grams. The filtrate and residue was subject to carbohydrate thin layer chromatography which revealed that both compositions were chemically similar having components at RF of about 0.55 and baseline residue.

A reverse-phase chromatography column was packed with 50 grams of $C_{18}$ coated support. The combined samples were placed on the column and washed with about 250 milliliters of water. The water collection was fraction 1. The column was washed with a 50 volume % methanol/water solution and the elution was collected in 5 equal fractions (fractions 2-6) totalling approximately 900 milliliters. Lastly, the column was washed with 100% methanol, collected in 4 fractions (fractions 7-10) totalling 600 milliliters. Fraction 3 appeared to have the maximum treatment activity and the minimum surface tension in aqueous solution of 50 milligrams of the material and 50 milliliters of water. The surface tension was about 50.6 dynes per centimeter. Unconverted distilled water measured 60.5 dynes/cm.

| Elemental Analyses (M-H-W Laboratories, Phoenix, Arizona): | | |
| --- | --- | --- |
| Element | Percent Calculated | Percent Found |
| C | 37.1 | 46.0 |
| H | 5.2 | 5.7 |
| O | 57.7 | 48.3 |

The compound was soluble in water, insoluble in methanol, and insoluble in ethyl acetate and chloroform. Treatment of the composition with pectinase changes its properties, implying a polygalacturonic acid sequence structure.

The infrared spectrum of the composition gave absorbences of the following wave numbers (cm$^{-1}$): 3400S, 2930M, 2110W, 1730M, 1620M, 1510M, 3810M, 1250M, 1150M, 1110M, 1040S, 805M, 700W, 6150W.

The $^1$H-NMR (proton magnetic resonance spectrum) of the polycyclogalacturonic acid compounds at 300 Megahertz is shown in FIG. 1. The proton spectrum was observed on a NICOLET magnetic resonance spectrophotometer on a solution (CA 0.5 milliliters of an approximate concentration of 50 milligrams per milliliters of the sample of the compound in a denatured water (D$_2$O) solvent. The spectrum was calibrated against an internal standard: DDS [3-(trimethylsilyl)-1-propane sulfonic acid, sodium salt)] and frequencies recorded in parts per million downfield from the standard.

The $^{13}$C-NMR spectrum of the compounds of the invention are shown in FIG. 2 of the Drawings. The $^{13}$C-NMR spectrum was observed on a Brooker UM-250 spectrometer on a solution (about 0.5 milliliters of an approximately 50 milligrams per milliliter solution of the sample of the compound in a D$_2$O:solvent). The spectrum was calibrated against an internal DDS standard and frequencies were recorded in parts per million downfield from the standard.

I believe that the compounds of this invention, through their secretion thinning and mobilizing effect, can be useful in treating the following conditions: hyaline membrane disease in infants for the purpose of increasing oxygen transfer over the hyaline membrane in newborns and premature infants; cystic fibrosis to loosen up the thick, heavy mucous that forms in the lungs; asthma; chronic bronchitis; chronic obstructive lung disease or emphysema; serious otitis media and sinus congestion and pneumonia.

Additionally, dermal conditions may benefit from this preparation for improving the softness and wrinkling of normal skin, reduction in the oiliness of skin, improvement in seborrhea, psoriasis and eczema.

The compositions of the invention appear to be attracted to surface characteristics. As a result, aqueous solutions of the composition tend to lose potency as the active ingredient tends to plate onto the surfaces of containers. Most successful topical preparations appear to be in the form of a zinc oxide preparation in a petroleum base. It appears that the zinc oxide cooperates with the polycyclogalacturonic acid composition to prevent separation and surface association.

The active compositions which have been tested comprise 500 milligrams of the cyclopolygalacturonic acid compounds formed in Example 1 in 99.5 grams of an ointment base containing 25 wt % zinc oxide, 25 wt % starch and 50 wt % white petroleum. Also tested was a preparation of the juniper berry containing the cyclopolygalacturonic acid compound prepared by boiling the crushed berries in a 50 wt % isopropyl alcohol solution, acidified by 4 wt % acetic and with a 2 wt % surfactant solution to assist filtration. The effect of both preparations are similar.

Case Studies

Case A

Case A is a 10 year old boy who has had blackheads on his nose for the past year. They are impossible to remove by hard scrubbing or by trying to press out. The substance was applied to his nose once daily in a zinc oxide vehicle. After three weeks the blackheads began to loosen and many were expressed spontaneously. At the fourth week the remainder, about half, were expressed manually. Little pressure was necessary to remove the remaining blackheads.

When application of the substance was discontinued, acne returned with blackheads, pimples, and pustules. His skin secretions thickened, and changed to a heavy oil or greasy character, and became difficult to wash off with soap and water. His skin had a bumpy and harsh texture. An application of the substance changed the secretions to a light oil texture, easy to wash off with soap and water, and the acne lesions receded. His skin texture became smooth.

Case B

Case B is a 13 year old boy with three years of acne vulgarous. Blackheads and pustules covered his forehead, cheeks and chin. His skin secretions were of a heavy oily or greasy character, and his skin a bumpy harsh texture. The substance was applied topically in a zinc oxide vehicle and within a week new pustules no longer erupted. His skin secretions were light oily and his skin texture smooth. By the third week most of the pustules had discharged themselves and new blackheads were not forming, old blackheads were beginning to spontaneously erupt. By the fourth week, there were few pustules and blackheads and most of the original pustules had disappeared or decreased to non-elevated red areas from which they would be expected to eventually disappear altogether.

Case C

Case C is a 15 year old boy with severe acne over the past three years. Previous treatment including topical agents and tetracycline were not effective in controlling the acne. Pustules and blackheads were found over his face and on his shoulders and back. His skin secretions were heavy oily or greasy and hard to wash off. His skin texture was harsh and bumpy.

The substance in zinc oxide was administered to the face and back. The first change noticed by the patient was a decrease in the greasy feeling of his face and a softening of the skin of the face and shoulders. Following this, no new pustules erupted nor new blackheads formed. By the third week, blackheads were beginning to erupt spontaneously and there was a great decrease in many of the earlier pustules. Many of the old pustules were flat and, by the fourth week, the redness was beginning to leave the area where the old pustules were.

Case D

Case D is an 18 year old boy with severe acne of four or five years duration. Pustules and blackheads covered his face and back. His secretions were heavy oily or greasy, his skin texture harsh and bumpy. Previous treatment with antibiotics and topical ointments had resulted in limited control.

The use of the substances in zinc oxide changed his skin secretions to light oily and easy to wash off. His skin texture became smooth. During this period no new pustules erupted and no new blackheads formed. By the third week, blackheads were beginning to erupt spontaneously and, by the fourth week, they were easy to express. During the third and fourth week the pustules had decreased in size and many of the old ones were flat and the red color in them was decreasing and vanishing.

Case E

Case E is a 49-year old male with mild acne which had been present since childhood. During childhood it had been severe. There were small blackheads on the face and papular eruptions on the back of the neck and back. His skin secretions were heavy oily or greasy and difficult to wash off, his skin texture harsh and bumpy.

The substance in zinc oxide was applied topically. During the first week, a marked change in the sensation of the skin was felt with the skin becoming much smoother and the feeling of heavy oiliness changing to a light oily feeling that was easily removed with washing. By the third week, many of the blackheads were beginning to erupt spontaneously and others were expressed easily. By the fourth week, the papular eruptions at the back of the neck had subsided and the face was clear of blackheads.

Our examples show that in each case, A to E, the good effect of my compounds began with the change in the character of skin secretions. Heavy oily or greasy secretions difficult to remove with soap and water washings changed to light oily secretions, more easily removed with soap and water. I believe a primary effect of my compounds is to allow thickened skin secretions, such as found in acne, to flow more easily from skin pores, allowing the unblocking of the sebaceous gland that leads to acne vulgaris. This same effect has been noted in in-vitro systems where the isolated compounds were added to water-oil solution and allowed the oil to disperse more readily in the water. Cases A to E examine the secretion changes in acne vulgaris but do not restrict this effect to this condition. This same secretion change will occur in patients with oily or greasy secretions and/or harsh bumpy skin texture without acne. Personal observation shows an enhancing effect of the flow of thickened secretions of the sinus cavities (as in people with sinus congestion) and chest (as in people with asthma) when the substance is ingested. I expect other conditions with thickened secretions, such as hyaline membrane disease and cystic fibrosis, to be similarly benefited.

Cases A to E have been treated with my compounds on many occasions. Unlike other agents that may have similar effects on secretions, the effect of juniper extract persists for several weeks after acne has improved and treatment stopped. I believe that this is due to the ability of the active principle to remain attached to the skin similar to the way it attaches to other surfaces such as glass and filter material.

I further believe that the skin texture changes from harsh bumpy to smooth results from the substance's effect on secretions. The light oily secretions noted in my cases lubricate the skin far more efficiently than the heavy oily or greasy secretions present prior to the use of the substance.

The substance appears to be absorbed into the skin surface where its effect is persistent and long lived. The substance is believed to cause a fundamental chemical change in oily secretions, resulting in greater ease of removal.

The above data, spectrum, examples and case studies provide a clear understanding of the efficacy, utility, and identity of the compounds of the invention. However, since many embodiments of the invention can be made without departing from the spirit and scope of the invention, the invention resides in the claims hereinafter appended.

I claim:

1. A process for recovering a crude secretion-changing composition active for oily skin, acne or other conditions, from a source of juniper berries which process comprises:
   (a) rupturing juniper berries;
   (b) extracting the crushed juniper berries with an extraction vehicle; and
   (c) recovering the crude composition.

2. The process of claim 1 wherein the juniper berries are mechanically ruptured.

3. The process of claim 1 wherein the extraction vehicle comprises deionized water at a temperature of about 50°-100° C.

4. The process of claim 1 wherein the crude anti-acne preparation can enhance the wetability of human skin or hair.

5. The process of claim 4 wherein the crude anti-acne preparation can enhance the wetability of human skin or hair and change its texture.

6. A powder anti-acne treatment composition comprising:
   (a) about 0.10-10 wt % of the product of claim 19; and
   (b) a major proportion of a powder support material capable of absorbing sebacious oils.

7. The powder treatment composition of claim 6 in the form of a compressed powder stick.

8. A liquid anti-acne treatment composition comprising:
   (a) about 0.1 to 10 wt % of the product of claim 19; and
   (b) a liquid diluent.

9. The composition of claim 8 wherein the liquid diluent comprises an aqueous diluent or an organic diluent.

10. The liquid treatment composition of claim 9 wherein the organic treatment diluent comprises a $C_{1-5}$ alkanol, acetone, ethylacetate, or mixtures thereof.

11. An anti-acne treatment composition in the form of a gel which comprises:
    (a) about 0.1-10 wt % of the product of claim 19;
    (b) an effective amount of the gelling agent; and
    (c) a major proportion of a diluent.

12. An aerosol spray anti-acne treatment composition which comprises:
    (a) about 0.1-10 wt % of a cyclopolygalacturonic acid compound; and
    (b) a volatile diluent.

13. The spray treatment composition of claim 12 wherein the composition additionally comprises a volatile propellant.

14. A process for recovering a crude secretion-changing composition active for oily skin, acne or other conditions, from a source of juniper berries which process comprises:
    (a) contacting ruptured juniper berries with an acidified aqueous alcoholic extraction medium containing about 0.01 to 5 wt % of a surface; and
    (b) separating the extraction medium containing the composition from the berries.

15. The process of claim 14 wherein the separation is by use of filtration.

16. The process of claim 14 wherein the aqueous alcoholic medium comprises an aqueous-isopropyl alcohol medium containing 10-90 wt % isopropyl alcohol.

17. The process of claim 14 wherein the medium is acidified with 4 wt % aqueous acetic acid.

18. The process of claim 14 wherein the surfactant is an anionic surfactant.

19. An anti-acne product comprising the product of the process of claim 5.

* * * * *

UNITED STATES PATENT AND TRADEMARK OFFICE
CERTIFICATE OF CORRECTION

PATENT NO. : 5,057,502
DATED : October 15, 1991
INVENTOR(S) : William E. Walsh It is certified that error appears in the above-identified patent and that said Letters Patent is hereby corrected as shown below:

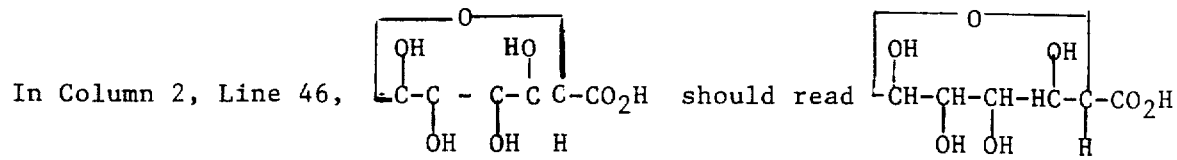

In Column 3, Line 30, insert --)-- after the letter "O", should read "O )—"

In Column 4, Line 67, "cyclopolyglucturonic" should read --cyclopolygalacturonic--.

In Column 9, Line 38, "polycyclogalacturonic" should read --cyclopolygalacturnoic--.

In Column 12, Line 51, "surface" should read --surfactant--.

Signed and Sealed this

Twenty-second Day of June, 1993

Attest:

MICHAEL K. KIRK

Attesting Officer

Acting Commissioner of Patents and Trademarks